(12) United States Patent
Dillon et al.

(10) Patent No.: US 9,436,868 B2
(45) Date of Patent: Sep. 6, 2016

(54) OBJECT CLASSIFICATION FOR MEASURED THREE-DIMENSIONAL OBJECT SCENES

(75) Inventors: Robert F. Dillon, Bedford, NH (US); Bing Zhao, Newton, MA (US)

(73) Assignee: Dimensional Photonics International, Inc., Wilmington, MA (US)

( * ) Notice: Subject to any disclaimer, the term of this patent is extended or adjusted under 35 U.S.C. 154(b) by 765 days.

(21) Appl. No.: 13/217,652

(22) Filed: Aug. 25, 2011

(65) Prior Publication Data

US 2012/0062716 A1    Mar. 15, 2012

Related U.S. Application Data

(60) Provisional application No. 61/381,731, filed on Sep. 10, 2010.

(51) Int. Cl.
| | | |
|---|---|---|
| A62B 1/04 | (2006.01) | |
| G06K 9/00 | (2006.01) | |
| A61C 9/00 | (2006.01) | |

(52) U.S. Cl.
CPC .......... *G06K 9/00201* (2013.01); *A61C 9/006* (2013.01); *G06K 2209/05* (2013.01)

(58) Field of Classification Search
USPC .......................................................... 348/66
See application file for complete search history.

(56) References Cited

U.S. PATENT DOCUMENTS

| | | | |
|---|---|---|---|
| 4,575,805 A | 3/1986 | Moermann et al. | |
| 5,440,393 A | 8/1995 | Wenz | |
| 5,651,675 A * | 7/1997 | Singer | 433/172 |
| 5,818,587 A | 10/1998 | Devaraj et al. | |
| 6,507,675 B1 * | 1/2003 | Lee et al. | 382/266 |
| 6,594,539 B1 | 7/2003 | Geng | |
| 6,674,880 B1 * | 1/2004 | Stork et al. | 382/128 |

(Continued)

FOREIGN PATENT DOCUMENTS

| | | |
|---|---|---|
| CN | 101617934 A | 4/2010 |
| JP | 06154251 | 6/1994 |

(Continued)

OTHER PUBLICATIONS

Office Action in related Japanese patent application No. 2011-195659, mailed on Jul. 30, 2013; 3 pages.

(Continued)

*Primary Examiner* — Tracy Li
(74) *Attorney, Agent, or Firm* — Schmeiser, Olsen & Watts LLP; William G. Goerin

(57) ABSTRACT

Described are methods that enable rapid automated object classification of measured three-dimensional object scenes. Each method can be performed during a three-dimensional measurement procedure while data are being acquired or after completion of the measurement procedure using the acquired data. In various embodiments, an object scene is illuminated with an optical beam and an image is acquired. In some embodiments, the object scene is illuminated with a structured light pattern and a sequence of images of the object scene illuminated by the pattern at different spatial phases is acquired. Coordinates are determined for points in the one or more images and a translucence value is determined for each of the points. An object class is determined for each point based on the translucence value for the point. Optionally, additional information, such as grayscale or color image data for each point, is used to supplement the object class determination.

7 Claims, 4 Drawing Sheets

(56) References Cited

U.S. PATENT DOCUMENTS

2002/0130873 A1* 9/2002 Takakura et al. ............. 345/473
2005/0234946 A1* 10/2005 Woo et al. .................... 707/100
2006/0079981 A1* 4/2006 Rubbert et al. ................ 700/98
2007/0076074 A1* 4/2007 Zhang et al. ................. 347/101
2009/0133260 A1 5/2009 Durbin et al.

FOREIGN PATENT DOCUMENTS

| | | |
|---|---|---|
| JP | 07-104458 | 4/1995 |
| JP | 09-135853 | 5/1997 |
| JP | 10-047936 | 2/1998 |
| JP | 2006191937 | 7/2006 |
| JP | 2008504049 | 2/2008 |
| JP | 2009-165831 | 7/2009 |
| WO | 2009139110 A1 | 11/2009 |
| WO | 2010099036 A1 | 9/2010 |

OTHER PUBLICATIONS

First Office Action in related Chinese patent application No. 201110273996.X, mailed on Dec. 4, 2013; 41 pages.

Office Action in related Japanese patent application No. 2011-195659, mailed on Dec. 4, 2012; 3 pages.

Extended European Search Report in related European patent application No. 11179804.7, mailed on Apr. 1, 2014; 8 pages.

Rawicz, et al., "Translucency measurements in teeth and dental materials", Proceedings of the International Society for Optical Engineering, vol. 4950, Jan. 1, 2003, pp. 259-265.

Brodbelt, et al., "Translucency of Human Dental Enamel", Journal of Dental Research, vol. 60, No. 10, Oct. 1, 2981, pp. 1749-1753.

Examination Report in related European Patent Application No. 11179804.7, mailed on Nov. 26, 2015; 5 pages.

\* cited by examiner

OBJECT CLASSIFICATION FOR MEASURED THREE-DIMENSIONAL OBJECT SCENES

RELATED APPLICATION

This application claims the benefit of the earlier filing date of U.S. Provisional Patent Application Ser. No. 61/381,731, filed Sep. 10, 2010 and titled "Method of Data Processing and Display for a Three-Dimensional Intra-Oral Scanner," the entirety of which is incorporated herein by reference.

FIELD OF THE INVENTION

The invention relates generally to three-dimensional imaging (3D) of an object scene. More particularly, the invention relates to a method of differentiating between different classes of objects in a 3D measurement of the object scene.

BACKGROUND OF THE INVENTION

In a typical dental or medical 3D camera or scanner imaging system, a series of two-dimensional (2D) intensity images of one or more object surfaces in an object scene is acquired where the illumination for each image may vary. In some systems, structured light patterns are projected onto the surface and detected in each 2D intensity image. For example, the projected light pattern can be generated by projecting a pair of coherent optical beams onto the object surface and the resulting fringe pattern varied between successive 2D images. Alternatively, the projected light pattern may be a series of projected parallel lines generated using an intensity mask and the projected pattern shifted in position between successive 2D images. In still other types of 3D imaging systems, techniques such as confocal imaging are employed.

In a dynamic 3D imaging system, a series of 3D data sets is acquired while the camera or scanner is in motion relative to the object scene. For example, the imaging system can be a wand or other handheld device that a user manually positions relative to the object scene. In some applications, multiple objects surfaces are measured by moving the device relative to the objects so that surfaces obscured from view of the device in one position are observable by the device in another position. For example, in dental applications the presence of teeth or other dental features in a static view can obscure the view of other teeth. A processing unit registers the overlapped region of all acquired 3D data to obtain a full 3D data set representation of all surfaces observed during the measurement procedure.

The results of a 3D measurement can be difficult to interpret. For example, measurements of an intra-oral cavity typically include 3D data for different classes of objects such as teeth, artificial dental structures and gingiva. The 3D data can be presented to a user in different graphical formats such as a display of the points in the form of a 3D surface map representation or in the form of a 3D point cloud. Differentiating between different structures represented in the display can be problematic and may require extensive effort to properly interpret features in the display. In some instances, the clinician may be unable to distinguish adjacent portions of separate objects. For example, it can be difficult for a dental professional to accurately recognize the boundary between gingiva and enamel or dentin.

SUMMARY

In one aspect, the invention features a method of object classification for images of an intra-oral cavity. The method includes illuminating at least a portion of an intra-oral cavity with an optical beam and acquiring an image of the illuminated portion. Coordinates are determined for a plurality of points in the image and a translucence value is determined for each of the points. An object class is determined for each of the points based on the translucence value of the point.

In another aspect, the invention features a method of object classification of 3D data for an object scene. The method includes illuminating an object scene with a structured light pattern and acquiring images of the illuminated object scene. Coordinates are determined for a plurality of points in the object scene based on the acquired images. A translucence value is determined for each point and an object class is determined for each point based on the translucence value of the point.

In still another aspect, the invention features a method of object classification of 3D data for an object scene. The method includes illuminating an object scene with a sequence of structured light patterns each having a different spatial phase. An image of the object scene is acquired for each of the structured light patterns. Coordinates are determined for a plurality of points in the object scene based on the acquired images. A background intensity value is determined for each point based on the acquired images and an object class is determined for each point based on the background intensity value for the point.

In still another aspect, the invention features an apparatus for object classification of an object scene. The apparatus includes an illumination source to illuminate an object scene, an imager and a processor in communication with the imager. The imager is configured to acquire an image of the illuminated object scene and to provide an output signal comprising 2D image data for the object scene. The processor is configured to determine a translucence value for a plurality of coordinates represented in the image in response to the 2D image data. The processor determines an object class for each of the coordinates in response to the translucence value for the coordinate.

In still another aspect, the invention features an apparatus for object classification of an object scene. The apparatus includes a projector, an imager and a processor in communication with the imager. The projector is configured to illuminate an object scene with a sequence of structured light patterns. The imager is configured to acquire an image of the illuminated object scene for each structured light patterns in the sequence. The imager provides an output signal comprising 2D image data for the object scene for each of the images. The processor is configured to determine 3D coordinates for the object scene and a translucence value for each of the 3D coordinates in response to the 2D image data for the sequence. The processor determines an object class for each of the 3D coordinates in response to the translucence value for the 3D coordinate.

BRIEF DESCRIPTION OF THE DRAWINGS

The above and further advantages of this invention may be better understood by referring to the following description in conjunction with the accompanying drawings, in which like numerals indicate like structural elements and features in the various figures. For clarity, not every element may be labeled in every figure. The drawings are not necessarily to scale, emphasis instead being placed upon illustrating the principles of the invention.

DETAILED DESCRIPTION

Figure 1:
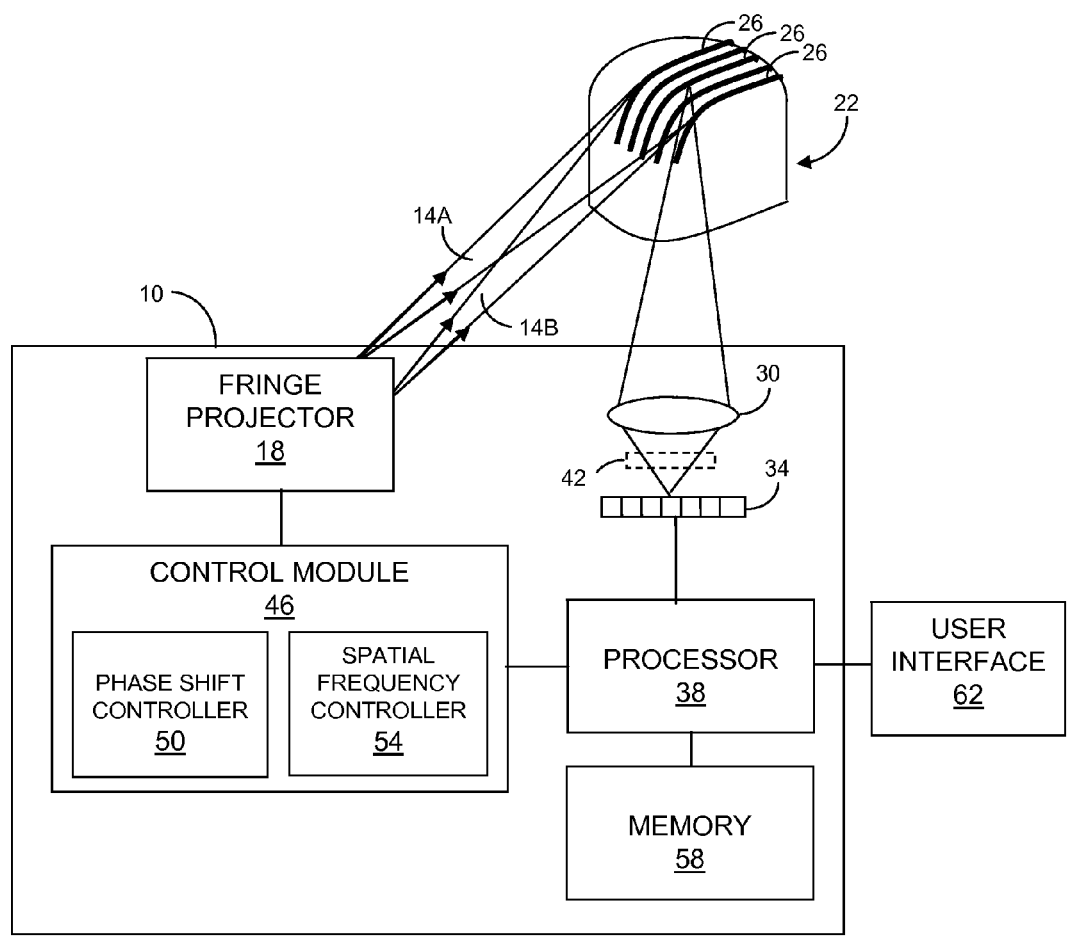
FIG. 1 is a block diagram showing an example of a measurement system that can be used to obtain a 3D image of an object scene.

The present teaching will now be described in more detail with reference to exemplary embodiments thereof as shown in the accompanying drawings. While the present teaching is described in conjunction with various embodiments and examples, it is not intended that the present teaching be limited to such embodiments. On the contrary, the present teaching encompasses various alternatives, modifications and equivalents, as will be appreciated by those of skill in the art. Those of ordinary skill in the art having access to the teaching herein will recognize additional implementations, modifications and embodiments, as well as other fields of use, which are within the scope of the present disclosure as described herein.

The methods of the present invention may include any of the described embodiments or combinations of the described embodiments in an operable manner. In brief overview, the methods of the invention enable rapid automated object classification of measured 3D object scenes. As used herein, object classification refers to the determination of a type or class of object from a plurality of possible object classes for a measured object. The method can be performed during the 3D measurement procedure while data are being acquired. Alternatively, the method can be performed after completion of a measurement procedure with previously acquired data. In various embodiments, an object scene is illuminated with an optical beam and an image is acquired. Coordinates are determined for points in the image and a translucence value is determined for each of the points. An object class is determined for each point based on the translucence value for the point. Optionally, grayscale or color image data for each point is used to supplement the object class determination.

In specific embodiments described below, the methods relate to object classification for 3D data during or after a 3D measurement of an oral cavity, such as a measurement made by a clinician in a dental application. Measured surfaces may include the enamel surface of teeth, the dentin substructure of teeth, gingiva, various dental structures (e.g., posts, inserts and fillings) and soft tissue (e.g., the tongue or lip). Classification of the 3D measurement data for the intra-oral measurement allows a distinction among the 3D data that correspond to these different object classes. The ability to distinguish among different types of objects allows the 3D measurement data to be displayed in a manner that shows the object class in the measured object scene. Moreover, 3D measurement data from objects not of interest can be managed accordingly. For example, motion of the tongue or lip through the measurement field of view in an intra-oral measurement application can cause data to be acquired from the interfering object. The unwanted data can be discarded or otherwise prevented from corrupting the measurement of the intended object scene, i.e., the teeth and gingiva. It will be appreciated that the methods can also be applied in medical applications and other applications in which 3D measurement data are acquired for object scenes having a plurality of object classes.

In some of the embodiments described below, 3D measurement systems use structured illumination patterns generated by interferometric fringe projection or other techniques. Imaging components acquire 2D images to determine coordinate information of points on the surface of objects based on the structured illumination of the objects.

U.S. Pat. No. 5,870,191, incorporated herein by reference, describes a technique referred to as Accordion Fringe Interferometry (AFI) that can be used for high precision 3D measurements based on interferometric fringe projection. AFI-based 3D measurement systems typically employ two closely-spaced coherent optical sources to project the interferometric fringe pattern onto the surface of the object. Images of the fringe pattern are acquired for at least three spatial phases of the fringe pattern.

FIG. 1 illustrates an AFI-based 3D measurement system 10 used to obtain 3D images of one or more objects 22. Two coherent optical beams 14A and 14B generated by a fringe projector 18 are used to illuminate the surface of the object 22 with a pattern of interference fringes 26. An image of the fringe pattern at the object 22 is formed by an imaging system or lens 30 onto an imager that includes an array of photodetectors 34. For example, the detector array 34 can be a two-dimensional charge coupled device (CCD) imaging array. An output signal generated by the detector array 34 is provided to a processor 38. The output signal includes information on the intensity of the light received at each photodetector in the array 34. An optional polarizer 42 is oriented to coincide with the main polarization component of the scattered light. A control module 46 controls parameters of the two coherent optical beams 14 emitted from the fringe projector 18. The control module 46 includes a phase shift controller 50 to adjust the phase difference of the two beams 14 and a spatial frequency controller 54 to adjust the pitch, or separation, of the interference fringes 26 at the object 22.

The spatial frequency of the fringe pattern is determined by the separation of two virtual sources of coherent optical radiation in the fringe projector 18, the distance from the virtual sources to the object 22, and the wavelength of the radiation. The virtual sources are points from which optical radiation appears to originate although the actual sources of the optical radiation may be located elsewhere. The processor 38 and control module 46 communicate to coordinate the processing of signals from the photodetector array 34 with respect to changes in phase difference and spatial frequency, and the processor 38 determines 3D information for the object surface according to the fringe pattern images.

The processor 38 calculates the distance from the imaging system 30 and detector array 34 to the object surface for each pixel based on the intensity values for the pixel in the series of 2D images generated after successive phase shifts of the fringe patterns. Thus the processor creates a set of 3D coordinates that can be displayed as a point cloud or a surface map that represents the object surface. The processor 38 communicates with a memory module 58 for storage of 3D data generated during a measurement procedure. A user interface 62 includes an input device and a display to enable an operator such as a clinician to provide operator commands and to observe the acquired 3D information in a near real-time manner. For example, the operator can observe a display of the growth of a graphical representation of the point cloud or surface map as different regions of the surface of the object 22 are measured and additional 3D measurement data are acquired.

Figure 2:
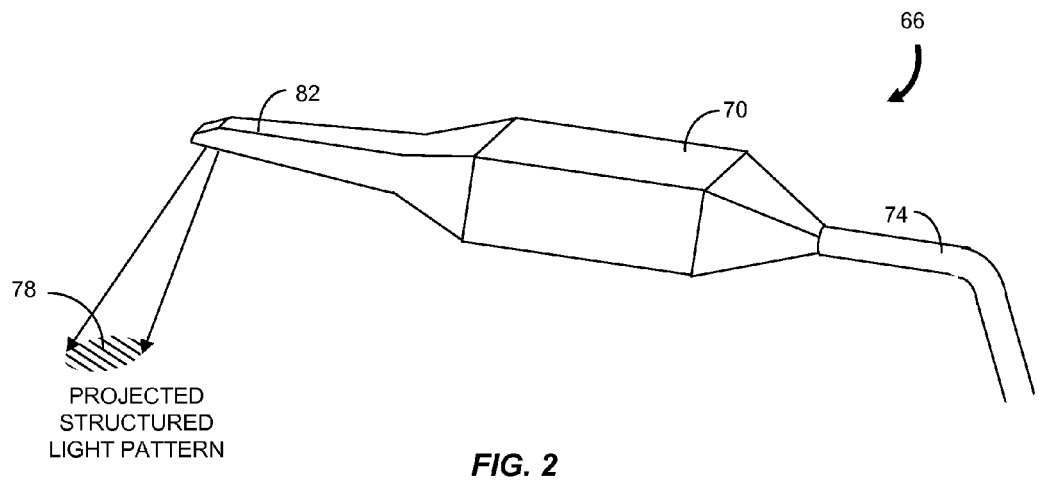
FIG. 2 illustrates a maneuverable wand that is part of a 3D measurement system used to obtain 3D measurement data for an intra-oral cavity.

FIG. 2 illustrates a handheld 3D measurement device in the form of a maneuverable wand 66 that can be used to obtain 3D measurement data for an intra-oral cavity. The wand 66 includes a body section 70 that is coupled through a flexible cable 74 to a processor and other system components (not shown). The wand 66 generates a structured light pattern 78 that is projected from near the projection end 82 to illuminate the object scene to be measured. For example, the structured light pattern 78 can be an interferometric fringe pattern based on the principles of an AFI measurement system as described above for FIG. 1. The wand 66 can be used to obtain 3D data for a portion of a dental arch. The wand 66 is maneuvered within the intra-oral cavity by a clinician so that 3D data are obtained for all surfaces that can be illuminated by the structured light pattern 78.

Figure 3:
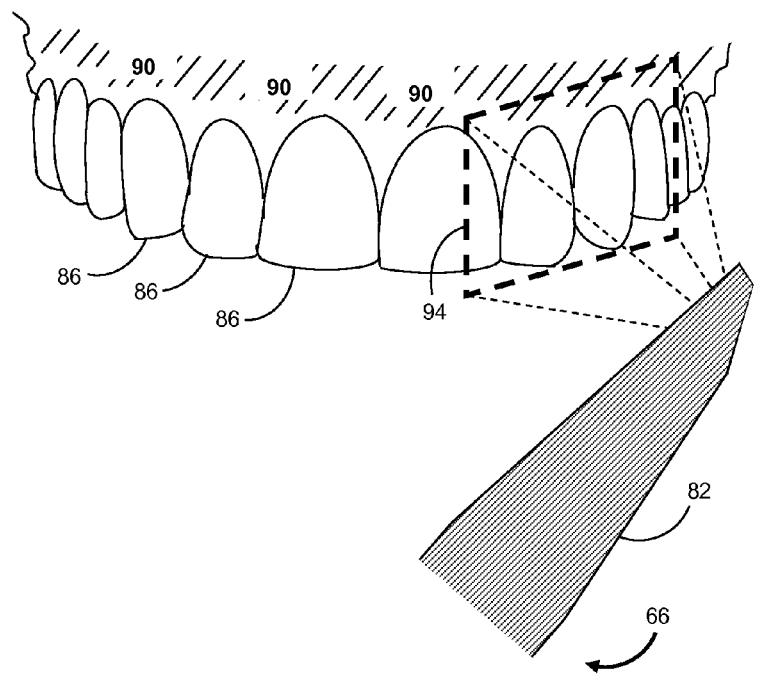
FIG. 3 illustrates how a 3D measurement of the upper dental arch is performed using the wand of FIG. 2.

FIG. 3 shows an example of how a 3D measurement of the upper dental arch is performed using the wand 66 of FIG. 2. In this example, the wand 66 is a maneuverable component of an AFI type 3D measurement system. Fringes are projected from the wand 66 onto the teeth 86 and adjacent gum tissue 90 in a measurement field of view 94 during a portion of a buccal scan of the dental arch. 3D data obtained from the measurement scan are displayed to the clinician preferably as a 3D point could or as a surface map (e.g., a wireframe representation) that shows the measured surfaces of the teeth 86 and gingiva 90.

Referring also to FIG. 1, the imaging array 34 receives an image of the fringe pattern projected onto the teeth 86 and adjacent gingiva 90 within the measurement field of view 94. Due to the translucent nature of the enamel, some of the light in the projected fringe pattern penetrates the surface of the teeth 86 and is scattered in a subsurface region. The scattered light typically results in degradation of the images of the fringe pattern. The degree of translucency determines the amount of light in the fringe pattern that penetrates the surface and is scattered below. If the scattered light contribution from the subsurface region is significant relative to the scattered light contribution from the fringe illumination at the surface, the apparent location (i.e., apparent phase) of the fringe pattern in the images can be different than the actual location of the fringe patterns on the surface of the teeth 86. Preferably, the fringe projector 18 uses an illumination wavelength that increases internal scatter near the surface. For example, the fringe illumination can include a near ultraviolet wavelength or shorter visible wavelength (e.g., from approximately 350 nm to 500 nm) which results in greater scatter near the surface and less penetration below the surface than longer wavelengths. In addition, the fringe pattern is preferably configured to have a high spatial frequency such that the light scattered from the shallow subsurface region results in a nearly uniform background light contribution to the images of the fringe patterns. During processing of the 2D images to determine the 3D data for the teeth 86, the background contribution from the subsurface region is ignored. Moreover, the magnitude of residual error induced by any spatially-varying intensity contribution from the subsurface region is less significant because the contribution is limited to a shallow region below the surface of each tooth 86. In an exemplary embodiment, the wavelength of the projected fringe pattern is 405 nm and the spatial frequency, or pitch, of the fringe pattern at the tooth surface is at least 1 fringe/mm.

Figure 4:
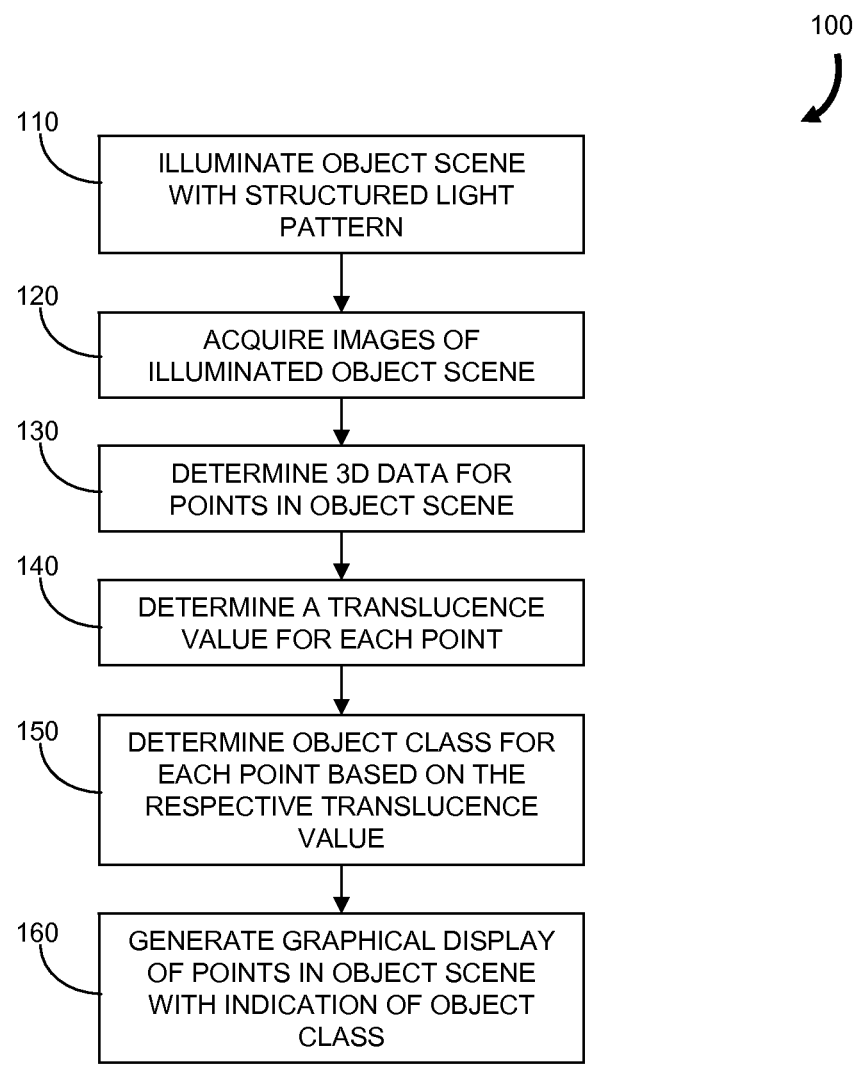
FIG. 4 is a flowchart representation of a method of classification of 3D data for an object scene according to an embodiment of the invention.

FIG. 4 is a flowchart representation of an embodiment of a method 100 of object classification for 3D data for an object scene. The method 100 includes illuminating (step 110) the object scene with a structured light pattern. By way of examples, the structured light pattern can be a striped intensity pattern generated by interference of coherent optical beams or shadow mask projection. Images of the illuminated object scene are acquired (step 120). In some applications the object scene corresponds to a measurement field of view of a 3D imaging device and a larger object scene is measured by maneuvering the device so that the measurement field of view includes other regions of the larger object scene. The coordinates of the 3D points on the surfaces of the object scene are determined (step 130) from the acquired images.

A translucence value for each measured 3D point is determined (step 140). The object scene can include objects that are distinguishable from each other. For example, two objects may be comprised of different materials that exhibit different translucence. Thus the translucence value can be used to determine (step 150) the type of object, or object class, for the point. Object classification can be based on comparing the translucence value to one or more threshold values associated with different types of objects. For example, the object classification can be based on determining which range in a plurality of ranges of translucence values includes the translucence value for the point. In this example, each range of translucence values corresponds to a unique object classification. Optionally, a reflectance value corresponding to the magnitude of the light scattered from the surface of a corresponding object is used in combination with the translucence value to determine the object class. In this case, the reflectance value is compared to reflectance threshold values or ranges of threshold values that are associated, in combination with the translucence values, with various object classes.

A graphical display of the object scene is generated (step 160). The display includes an indication of the object class for each of the points. For example, the display can be a 3D surface map representation where a wireframe representation, surface element depiction or the like is displayed with different colors to indicate the object classes. Other graphical parameters can be used to indicate the object classification for each point. In another example, the display can be a 3D point cloud where each point has a color associated with its object classification. In some embodiments, the graphical display can include boundary lines or similar features to segment or differentiate different regions of the object scene into graphical objects so that different objects can easily be recognized.

Optionally, a color image of the illuminated region of the object scene is acquired. The color data acquired for each point can be used in combination with the translucence value for the point to make the determination of the object class for the point. The color image can be acquired under passive lighting or a supplemental light source such as a white light source or broadband light source can be used to improve the ability to perform differentiation by color. In an alternative embodiment, sequential operation of spectral light sources such as red, green and blue light emitting diodes (LEDs) can be used to generate RGB images. In this manner, a monochromatic imager can be used to generate the color data to supplement the object classification.

In an alternative option, a grayscale image of the illuminated region of the object scene is acquired. The object grayscale value for each point is used in combination with the translucence value for the point to determine the object class for the point. The grayscale image may be acquired with passive lighting or a supplemental light source can be utilized.

Figure 5:
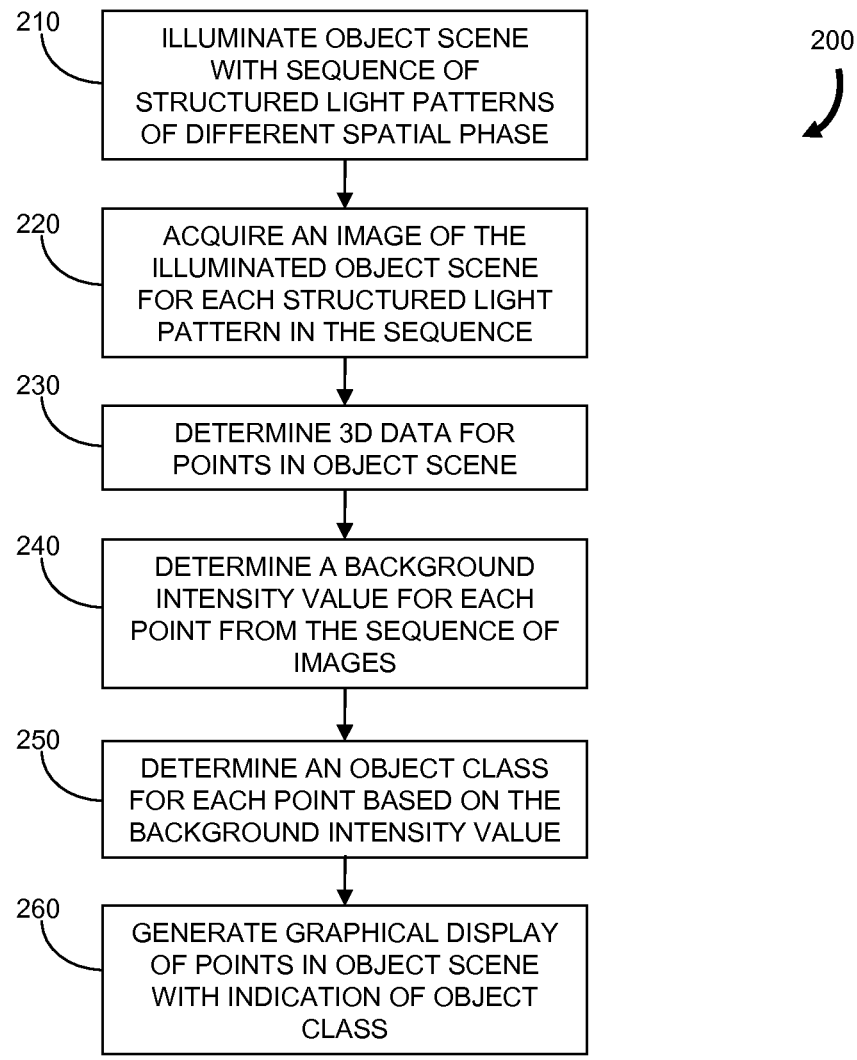
FIG. 5 is a flowchart representation of a method of object classification of 3D data for an object scene according to another embodiment of the invention.

FIG. 5 is a flowchart representation of an embodiment of a method 200 of object classification of 3D data for an object scene. The method 200 includes illuminating (step 210) an object scene with a sequence of structured light patterns of different spatial phase. Preferably, the structured light patterns are interferometric intensity patterns having a sinusoidal intensity variation in one dimension. The sinusoidal intensity pattern is generated, for example, by the interference of two coherent beams as described above with respect to FIG. 1. Preferably, the sequence includes a set of three sinusoidal intensity patterns each having a spatial phase that is offset from the other two sinusoidal intensity patterns by 120°.

An image of the illuminated object scene is acquired (step 220) for each of the light patterns in the sequence. 3D data are determined (step 230) for points in the object scene based on the images of the sequence of structured light patterns.

A background intensity value is calculated (step 240) for each point from the sequence of images. In general, the background intensity value for a point in the object scene is primarily due to the translucence of the object associated with the point if other sources of illumination of the object scene are maintained at low levels and if the image acquisition time is sufficiently small. Thus the background intensity value can be used as a measure of the translucency (i.e., a translucence value) for the point. In an embodiment based on the projection of the three sinusoidal intensity patterns, the background intensity value for a point is determined by first mathematically fitting a sinusoidal intensity variation to the three intensity values for the location of the point in the 2D image of the illuminated object scene. For example, the mathematical fitting can be a least squares fit of a sinusoidal function. The background intensity is present in all the images of the sequence and degrades the contrast. The value of the background intensity is determined as the minimum value of the fitted sinusoidal function.

As the background intensity value is closely related to the translucence value, the background intensity level can be used to determine (step 250) the type of object, or object class, for the point, for example, by comparing the background intensity value to one or more threshold values or background intensity value ranges associated with different types of objects. In a further embodiment, object classification is a two-step comparison in which object classification also includes comparing the maximum of the fitted sinusoidal function to one or more threshold intensity values.

A graphical display of the object scene is generated (step 260) and includes an indication of the object class for each of the points. The display can be any type of surface map representation or a 3D point cloud, as described above with respect to the method of FIG. 4, in which color or other graphical features are used to indicate different object classes and structures. Optionally, color or grayscale images of the object scene are acquired and used in combination with the background intensity values to make the determinations of the object classes.

Although the embodiments described above relate primarily to object classification in which the object scene is illuminated using a structured light pattern, it will be recognized that object classification by determination of translucence can be performed under more general illumination conditions. For instance, the object scene can be illuminated with an optical beam in any manner that allows the translucence value for points or regions on the object to be determined. Optical coherence tomography (OCT) systems and confocal microscopy systems are examples of measurement systems that can be adapted for translucence measurement and object classification. The characteristics of the optical beam, such as wavelength or spectral width, can be chosen to best assist in discriminating between different object classes. Moreover, grayscale or color image data for the object scene can be utilized in various embodiments to improve the object classification capability.

While the invention has been shown and described with reference to specific embodiments, it should be understood by those skilled in the art that various changes in form and detail may be made therein without departing from the spirit and scope of the invention as recited in the accompanying claims.

What is claimed is:

1. A method of object classification for images of an intra-oral cavity, comprising:
    illuminating at least a portion of an intra-oral cavity with an optical beam;
    acquiring, at an imager having an array of photodetectors, an image of the illuminated portion of the intra-oral cavity;
    determining, at a processor, coordinates for a plurality of points in the image;
    determining, from the image, a background intensity value for each of the points;
    determining, at the processor, a translucence value for each of the points based on the determined background intensity value for each of the points; and
    determining, at the processor, an object class for each of the points based on the translucence value of the point, the object class selected from the group consisting of soft oral tissue, gingiva, teeth, posts, inserts, and cavity fillings.

2. The method of claim 1 wherein determining the object class for each point comprises comparing the translucence value to at least one threshold value associated with an object class.

3. The method of claim 1 further comprising determining, at the processor, an object color for each point and wherein determining the object class for each point is based on the translucence value and the object color.

4. The method of claim 1 further comprising determining, at the processor, an object grayscale value for each point and wherein determining the object class for each point is based on the translucence value and the object grayscale value.

5. The method of claim 1 wherein the coordinates are 3D coordinates for object surfaces in the intra-oral cavity.

6. The method of claim 1 wherein the coordinates are 2D coordinates for the image of the intra-oral cavity.

7. The method of claim 1 wherein determining the background intensity for each point comprises:
    fitting an intensity function to a portion of the image including the point; and
    determining a minimum value of the fitted intensity function.

* * * * *